United States Patent [19]
Gerecke et al.

[11] B 3,996,229
[45] Dec. 7, 1976

[54] 1-[10,11-DIHYDRO-DIBENZO[B,F]-THIE-PIN-10-YL]-4-(ALKYNYLALKYL)-PIPERA-ZINES

[75] Inventors: Max Gerecke, Reinach, Switzerland; Jean-Pierre Kaplan, Les Plessis Robinson, France; Emilio Kyburz, Reinach, Switzerland

[73] Assignee: Hoffmann-La Roche Inc., Nutley, N.J.

[22] Filed: Jan. 8, 1975

[21] Appl. No.: 539,374

[44] Published under the second Trial Voluntary Protest Program on March 9, 1976 as document No. B 539,374.

[30] Foreign Application Priority Data

Jan. 14, 1974 Switzerland .................. 449/74
Nov. 15, 1974 Switzerland .................. 15249/74

[52] U.S. Cl. .................. 260/268 TR; 260/327 B; 424/250
[51] Int. Cl.² .............. C07D 295/10; C07D 295/12
[58] Field of Search .............................. 260/268 TR

[56] References Cited
UNITED STATES PATENTS

| | | | |
|---|---|---|---|
| 3,351,599 | 11/1967 | Protiva et al. | 260/268 TR |
| 3,379,729 | 4/1968 | Protiva et al. | 260/268 TR |
| 3,600,391 | 8/1971 | Mastursi et al. | 260/268 TR |
| 3,725,409 | 4/1973 | Protiva et al. | 260/268 TR |

FOREIGN PATENTS OR APPLICATIONS

| | | |
|---|---|---|
| 2,223,039 | 10/1974 | France |
| 2,026,027 | 12/1970 | Germany |
| 6,814,346 | 4/1969 | Netherlands |

Primary Examiner—Richard J. Gallagher
Assistant Examiner—Jose Tovar
Attorney, Agent, or Firm—Samuel L. Welt; Bernard S. Leon; William G. Isgro

[57] ABSTRACT

Dibenzo[b,f]thiepin derivatives of the formula

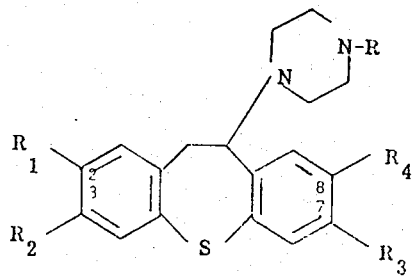

wherein R, $R_1$, $R_2$, $R_3$ and $R_4$ are as hereinafter set forth, are described. The dibenzo[b,f]thiepins of the invention possess strong central depressant and neuroleptic properties and are therefore useful, for example, in the treatment of acute or chronic schizophrenia and also as tranquilizers.

4 Claims, No Drawings

1-[10,11-DIHYDRO-DIBENZO[b,f]-THIEPIN-10-YL]-4-(ALKYNYLALKYL)-PIPERAZINES

BRIEF SUMMARY OF THE INVENTION

The invention relates to dibenzo[b,f]thiepin derivatives of the formula

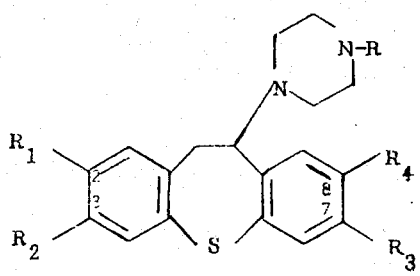

wherein R is lower alkynylalkyl, hydroxy-lower alkylalkynylalkyl or alkanoyloxy-lower alkylalkynylalkyl, and one of the two symbols $R_1$ and $R_2$ or $R_3$ and $R_4$ is hydrogen and the other is halogen, methyl, methoxy, methylthio trifluoromethyl, methanesulfonyl or dimethylsulfamoyl, or pharmaceutically acceptable acid addition salts thereof.

DETAILED DESCRIPTION OF THE INVENTION

The dibenzo[b,f]thiepin derivatives of the invention are compounds of the formula

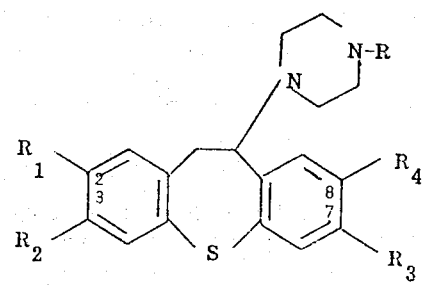

wherein R is lower alkynylalkyl, hydroxy-lower alkylalkynylalkyl or alkanoyloxy-lower alkylalkynylalkyl, and one of the two symbols $R_1$ and $R_2$ or $R_3$ and $R_4$ is hydrogen and the other is halogen, methyl, methoxy, methylthio, trifluoromethyl, methanesulfonyl or dimethylsulfamoyl, or pharmaceutically acceptable acid addition salts thereof.

From the foregoing definitions, it will be evident that the compounds of formula I each carry one substituent in each of the two aromatic nuclei, namely, in the 2- or 3-position and in the 7- or 8-position.

As used herein, the term "lower alkynylalkyl" denotes a straight-chain or branched-chain aliphatic group containing a triple bond and preferably containing 3 to 6 carbon atoms. Stated differently, the term "lower alkynylalkyl" means that the lower alkynyl group is linked via an alkyl (alkylene) group which may be alkylated. Examples of such groups are:

$-CH_2-C \equiv CH$ (2-Propynyl)

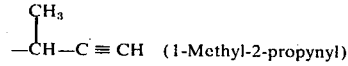

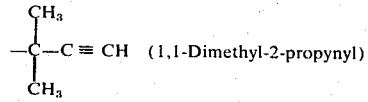

$-CH_2-C \equiv C-CH_3$ (2-Butynyl)

$-CH_2-CH_2-C \equiv CH$ (3-Butynyl)

$-CH_2-CH_2-CH_2-CH_2-C \equiv CH$ (5-Hexynyl)

$-CH_2-CH_2-C \equiv C-CH_2-CH_3$ (3-Hexynyl).

The term "hydroxy-lower alkylalkynylalkyl" denotes a straight-chain or branched chain group and preferably containing 4 to 6 carbon atoms. By definition, therefore, the triple bond is present neither immediately after the linkage position nor at the end of the group. Stated differently, the "hydroxy-lower alkylalkynylalkyl" is always linked via an alkyl (alkylene) group which may be alkylated and terminate with a hydroxyalkyl group which may be alkylated. Examples of such groups are:

$-CH_2-C \equiv C-CH_2-OH$ (4-Hydroxy-2-butynyl)

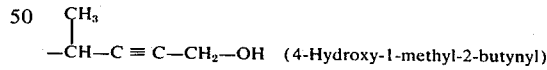

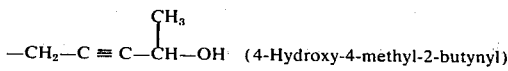

$-CH_2-CH_2-C \equiv C-CH_2-CH_2-OH$ (6-Hydroxy-3-hexynyl).

The term "alkanoyloxy-lower alkylalkynylalkyl" denotes a hydroxy-lower alkylalkynylalkyl group as defined hereinbefore in which the hydroxy group has been replaced by an alkanoyloxy group. The "alkanoyloxy" contains from 2 to 18 carbon atoms and can be straight-chain or branched-chain. Examples of such alkanoyloxy groups are acetoxy, pivaloyloxy, n-pentanoyloxy, or the like. The preferred alkanoyloxy groups are the long-chain alkanoyloxy groups, namely, those containing from 6 to 18 carbon atoms such as hexanoyloxy, heptanoyloxy, octanoyloxy, nonanoyloxy, decanoyloxy, undecanoyloxy, dodecanoyloxy, tetradecanoyloxy, hexadecanoyloxy, octadecanoyloxy, or the like.

The term "halogen" denotes fluorine, chlorine, bromine and iodine. Chlorine and fluorine are preferred.

The dibenzo[b,f]thiepin derivatives of formula I of the invention possess strong central depressant and neuroleptic properties. Accordingly, they may be used, for example, for the treatment of acute or chronic schizophrenia and also as tranquilizers. Advantageously, the compounds of formula I lack any significant side effects. Thus, for example, they have slight toxicity and no, or only slight, cataleptic side effects, that is, only insignificant motor disorders occur. Because of their advantageous activity, especially preferred dibenzo[b,f]thiepin of formula I are those wherein R is 2-propynyl or salts thereof with pharmaceutically acceptable acids. Particularly preferred dibenzo[b,f]thiepins of formula I are 1-[10,11-dihydro-3-methoxy-8-methylthio-benzo[b,f]thiepin-10-yl]-4-(2-propynyl)-piperazine, 1-[8-chloro-10,11-dihydro-3-methoxy-dibenzo[b,f]thiepin-10-yl]-4-(2-propynyl)-piperazine or salts thereof with pharmaceutically acceptable acids.

The dibenzo[b,f]thiepin derivatives of the invention, that is, the compounds of formula I and their salts with pharmaceutically acceptable acids are prepared by:

a. reacting a compound of the formula

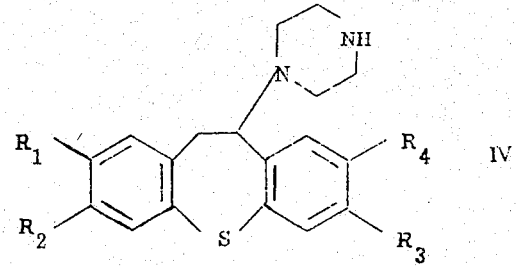

wherein $R_1$-$R_4$ are as previously described, with a compound yielding the group R, or c. for the preparation of a compound of formula I wherein R is alkanoyloxy-lower alkylalkynylalkyl, reacting a compound of the formula

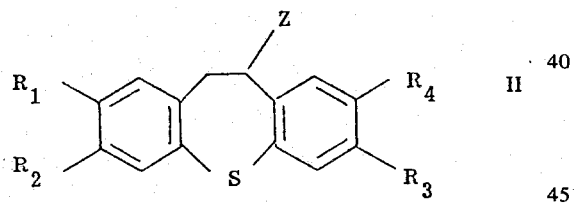

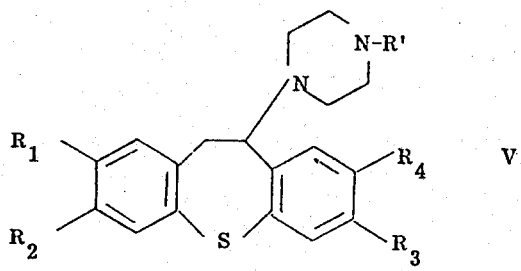

wherein $R_1$-$R_4$ are as previously described, and Z is a leaving atom or group, with a compound of the formula

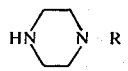

wherein R is as previously described, or b. reacting a compound of the formula wherein $R_1$-$R_4$ are as previously described, and R' is hydroxy-lower alkylalkynylalkyl, with an alkanecarboxylic acid or a reactive derivative thereof, and, if desired, converting the product obtained into a desired salt.

The leaving atom or group denoted by Z in the starting materials of formula II preferably is a halogen atom or an alkyl- or aryl-substituted sulfonyloxy group. The alkyl or aryl groups present in these substituted sulfonyloxy groups are preferably lower alkyl, especially methyl, or lower aryl, especially phenyl or tolyl. When Z is a halogen atom, chlorine or bromine is preferred.

The starting materials of formula II can be prepared according to known methods. For example, the atom or group denoted by Z in its various meanings can be introduced as follows:

Z = halogen: The corresponding 10-oxo compound is converted by reduction, for example, using sodium borohydride, into the 10-hydroxy compound and the latter reacted with a suitable halide, for example, thionyl chloride or thionyl bromide, or with a hydrohalide in the presence of a water-binding agent, such as hydrogen chloride, calcium chloride, or the like.

Z = alkyl- or aryl-substituted sulfonyloxy: The correspondng 10-hydroxy compound is reacted with an alkyl- or aryl-substituted sulfonic acid halide, for example, a chloride.

The starting materials of formula III can be prepared, for example, as set forth below, wherein in formulas VI, VII, VIII and III, Z and R are as previously described and $R_5$ is a suitable protecting group, for example, tosyl or benzyloxycarbonyl. More particularly, the compounds of formula III are prepared by the condensation of a compound of the formula

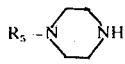　　　　　　VI with a compound of the formula

　　　　　　VII which is preferably carried out in the presence of an acid-binding agent, for example, potassium carbonate, triethylamine, or the like. The protecting group denoted by $R_5$ is subsequently removed from the condensation product of the formula

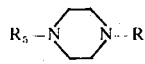　　　　　　VIII and yields the compound of the formula

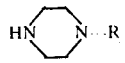　　　　　　III

The tosyl group can be removed by treatment with an alkali metal, for example, sodium, in liquid ammonia and the benzyloxycarbonyl group can be removed by acid cleavage using, for example, hydrogen bromide in glacial acetic acid.

The reaction of a compound of formula II with a compound of formula III in accordance with process embodiment (a) can be carried out in the absence of a solvent. However, when a solvent is used, it is conveniently an organic solvent, for example, an aromatic hydrocarbon such as benzene or toluene; a lower alkanol such as methanol or ethanol; a chlorinated hydrocarbon such as methylene chloride, trichloroethylene, chloroform, carbon tetrachloride or chlorobenzene; and aliphatic or cyclic ether such as diethyl ether, tetrahydrofuran or dioxane; dimethylformamide; or dimethylsulfoxide. The reaction is conveniently carried out at a temperature in the range of from about 30°C. to about 200°C., preferably at a temperature in the range of from about 60°C. to 150°C. The reaction is advantageously carried out in the presence of an acid-binding agent, for example, in the presence of an alkali carbonate such as potassium carbonate, or in the presence of an excess of the starting material of formula III.

The starting materials of formula IV can be prepared, for example, by reacting a compound of formula II with a mono-N-protected piperazine such as N-carbethoxypiperazine. The reaction product is subsequently subjected to an alkaline saponification, for instance, using an aqueous alkali.

The compounds yielding the group R, which are used in the reaction with the starting materials of formula IV, can be, for example, compounds of formula VII, namely, compounds of the formula R-Z, wherein R is as previously described and Z is a leaving atom or group. Examples of such compounds are 2-propynyl bromide, 3-butynyl chloride, 2-propynyl mesylate, 4-chloro-2-butyn-1-ol, 4-tosyl-2-butyn-1-ol, and the like. The reaction of such a compound with a starting material of formula IV in accordance with process embodiment (b) is conveniently carried out in an inert organic solvent, for example, an aromatic hydrocarbon such as benzene or toluene; a chlorinated hydrocarbon such as chloroform; an ether such as dioxane or dimethoxyethane; a lower alkanol such as methanol, ethanol, or butanol; a ketone such as acetone or methyl ethyl ketone; dimethylformamide; or dimethylsulfoxide. The reaction is preferably carried out at a temperature in the range of from about room temperature to about the boiling point of the reaction mixture. The reaction is preferably carried out in the presence of an acid-binding agent, for example, an alkali metal carbonate such as sodium carbonate or potassium carbonate, or an inert organic base such as triethylamine. An excess of the base of formula IV may also be used as the acid-binding agent.

Other compounds yielding the group R which are suitable for the reaction with the starting materials of formula IV are the corresponding Mannich reagents, for example, a lower aliphatic keto compound such as formaldehyde, acetaldehyde or acetone, together with an acetylene compound of the formula

　　　　　　IX wherein $R_6$ is hydrogen, hydroxy-lower alkyl, or alkanoyloxy-lower alkyl.

The aforementioned reagents are preferably used in about equimolar amounts up to a sight molar excess based upon the starting material of formula IV. The reaction is preferably carried out in an inert polar organic solvent, for example, dioxane or a lower alkanol such as ethanol, preferably under the catalytic influence of an inorganic heavy metal salt, for example, cuprous chloride or ferric chloride. The reaction is preferably carried out at a temperature in the range of from about room temperarture to the boiling point of the reaction mixture, preferably at about 100°C. In accordance with this reaction, there are obtained compounds of formula I, wherein R is a group of the formula

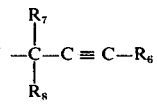

wherein $R_6$ is as previously described, and $R_7$ and $R_8$, independently, are hydrogen or lower alkyl.

The esterification of an alcohol starting material of formula V in accordance with process embodiment (c)

is preferably carried out by heating the starting material to about 50°–150°C. with a reactive derivative of the corresponding alkanecarboxylic acid, for example, an acid chloride or acid anhydride. The esterification can also be carried out by reaction with an alkanecarboxylic acid in the presence of a strong acidic catalyst, for example, sulfuric acid or p-toluenesulfonic acid, or in the presence of a water-entraining or water-binding agent, for example, dicyclohexylcarbodiimide or carbonyldiimidazole. The esterification is preferably carried out in an organic solvent, for example, benzene, toluene or pyridine.

Bases of formula I form pharmaceutically acceptable acid addition salts with inorganic acids, for example, hydrohalic acids such as hydrochloric acid, hydrobromic acid or hydroiodic acid, or with other mineral acids such as sulfuric acid, phosphoric acid and nitric acid, and with organic acids, for example, tartaric acid, citric acid, camphorsulfonic acid, methanesulfonic acid, toluenesulfonic acid, salicyclic acid, ascorbic acid, maleic acid, mandelic acid or the like. The preferred salts are the hydrohalides, especially the hydrochlorides, the maleates and the methanesulfonates. The acid addition salts are preferably prepared in a suitable solvent, for example, ethanol, acetone or acetonitrile, by treating the free base with an appropriate non-aqueous acid. Depending on the molar ratio between the free base and the acid, there is obtained, because of the two nitrogen atoms on the piperazine moiety, a salt containing one or two mols of acid per mol of base, that is, a mono or di salt. In the working-up of a di salt that is obtained, the corresponding di or mono salt is obtained, depending on the solubility of the mono or di salt in the solvent used.

The bases of formula I are partly crystalline, solid substances which have a relatively good solubility in dimethylsulfoxide, dimethylformamide, chlorinated hydrocarbons such as chloroform or methylene chloride, aromatic hydrocarbons such as benzene or toluene, and alkanols such as methanol or ethanol, and relatively insoluble in water.

The pharmaceutically acceptable acid addition salts of the bases of formula I are crystalline solid substances. They have a relatively good solubility in dimethylsulfoxide, dimethylformamide or alkanols such as methanol or ethanol, and are partly soluble in chloroform, methylene chloride or water. They are relatively insoluble in benzene, ether or petroleum ether.

In order to demonstrate the advantageous pharmacological activity of the dibenzo[b,f]thiepin derivatives of formula I of the invention, the following representative derivatives were tested:

Derivative A: 1-[10,11-Dihydro-3-methoxy-8-methylthio-dibenzo[b,f]thiepin-10-yl]-4-(2-propynyl)-piperazine dihydrochloride.

Derivative B: 1-[8-Chloro-10,11-dihydro-3-methoxy-dibenzo[b,f]thiepin-10-yl]-4-(2-propynyl)-piperazine dimethanesulfonate.

Chlorpromazine, a recognized central depressant or neuroleptic agent, was used as the standard.

The neuroleptic properties of the foregoing derivatives were determined numerically on the basis of the following test, i.e., the "pole climbing" test.

I. "Pole Climbing" Test

This test provides information about the behavior reaction of rats. Rats are trained to avoid, by climbing up a vertical pole in the test chamber, an electrical impulse—unconditioned impulse—released via the wire-latticed floor some seconds after an acoustic signal—conditioned impulse—.

The blocking of the conditioned reaction is designated by the parameter $ED_{50}$ (mg/kg p.o.) and the blocking of the unconditioned reaction is designated by the parameter $ED_{10}$ (mg/kg p.o.).

The parameter $ED_{50}$—blocking of the conditioned reaction—provides a measure of the neuroleptic activity strength of the derivative under investigation since, with falling value, the neuroleptic activity strength increases. The quotient $ED_{10}$—blocking of the unconditioned reaction-/$ED_{50}$—blocking of the conditioned reaction—gives a measure of the quality of action of the derivative under investigation since, when the quotient increases, a greater selectivity of the neuroleptic action, that is, slighter neurotoxic side-effects, is present.

Results:

| Derivative | $ED_{50}$ (blocking of the conditioned reaction) mg/kg p.o. | Quotient $ED_{10}$ (blocking of the unconditioned reaction)/ $ED_{50}$ (blocking of the conditioned reaction) |
|---|---|---|
| A | 17 | 9 |
| B | 25 | 4 |
| Chlorpromazine | 11.8 | 2.5 |

In this test, chlorpromazine has a somewhat stronger activity than Derivative A and Derivative B, but it is clearly inferior having regard to the quality (selectivity) of the neuroleptic activity of Derivative A and Derivative B.

In order to demonstrate the lack of any significant cataleptic side-effects, the following test was carried out:

II. Catalepsy Test

A cataleptic activity—"wax rigidity", i.e., abnormally long retention of a fixed body position—in central depressant or neuroleptically-active compounds is considered to be an undesirable side-effect produced by motor disorders. Representative dibenzo[b,f]thiepin derivatives of this invention were administered intraperitoneally to rats. The animals are considered to be cataleptic when the homolateral extremities remain in a crossed position for at least 10 seconds. The number of cataleptic animals is noted every 30 minutes for 6 hours. The $ED_{50}$ is that dose at which 50% of the animals show catalepsy.

Results:

| Derivative | $ED_{50}$ mg/kg |
|---|---|
| A | 88 |
| B | >100 |
| Chlorpromazine | 6 |

The foregoing Table shows that Derivatives A and B exhibit only very slight or no cataleptic side-effects. This is in contrast to chlorpromazine which shows a considerably greater cataleptic activity.

III. Toxicity

The tested derivatives possess a slight toxicity which will be evident from the following values for the acute toxicity in the mouse. The values relate to a duration of activity over a period of 24 hours:

| Derivative | LD$_{50}$ mg/kg p.o. |
|---|---|
| A | 900 |
| B | 750 |
| Chlorpromazine | 200 |

Chlorpromazine is clearly inferior to Derivatives A and B as regards toxicity.

The dibenzo[b,f]thiepin derivatives provided by the present invention can be used as medicaments, for example, in the form of pharmaceutical preparations which contain them in association with a compatible pharmaceutical carrier. Such a carrier can be an organic or inorganic inert carrier material suitable for enteral, for example, oral, or parenteral administration, for example, water, gelatin, lactose, starch, magnesium stearate, talc, vegetable oils, gum arabic, polyalkyleneglycols, or the like. The pharmaceutical preparations can be made up in solid form, for example, as tablets, dragees, suppositories or capsules, or in liquid form, for example, as solutions, suspensions or emulsions. The pharmaceutical preparations may be sterilized and/or may contain adjuvants such as preservatives, stabilizers, wetting agents, emulsifiers, salts for variation of the osmotic pressure or buffers. They may also contain other therapeutically valuable substances.

Pharmaceutical dosage forms can contain about 1 to 200 mg. of a compound of formula 1 or of one of its pharmaceutically acceptable acid addition salts. Convenient oral dosages comprise from about 0.1 mg.kg. per day to about 7.5 mg/kg per day. Convenient parenteral dosages are in the range of from about 0.01 mg/kg per day to about 0.75 mg/kg. per day. However, the foregoing ranges can be increased or decreased according to individual requirements.

The following Examples further illustrate the invention. All temperatures are in degrees Centigrade, unless otherwise states.

EXAMPLE 1

Preparation of 1-[10,11-dihydro-3-methoxy-8-methylthio-dibenzo[b,f]thiepin-10-yl] -4-(2-propynyl)-piperazine 12.0 G. of 10-chloro-10,11-dihydro-3-methoxy-8-methylthio-dibenzo[b,f]thiepin are heated under reflux for 12 hours together with 25 g. of N-(2-propynyl)piperazine in 60 ml. of chloroform. The reaction can also be carried out partially without the addition of a solvent, the reagents then being heated for about 10 minutes at an external temperature of 120°–130°C. After cooling, the mixture is poured on to water and extracted with ether. The organic phase is washed with water and subsequently treated with 2-N hydrochloric acid, whereby a precipitate forms. The entire mixture is washed with ether, made alkaline and subsequently extracted with ether. The organic phase is washed with water, dried over sodium sulfate and evaporated. The residue obtained is chromatographed over aluminum oxide with toluene, and the resulting 1-[10,11-dihydro-3-methoxy-8-methylthio-dibenzo-[b,f]thiepin-10-yl]-4- (2-propynyl)-piperazine is converted into the dihydrochloride by treatment with hydrogen chloride. The dihydrochloride melts at 195°–197°C.

The 10-chloro-10,11-dihydro-3-methoxy-8-methylthio-dibenzo[b,f]thiepin used as the starting material can be prepared as follows:

150 G. of 4-methoxy-anthranilic acid are suspended at 0°C. in 2 liters of water and 80 ml. of concentrated hydrochloric acid. A solution of 62 g. of sodium nitrite in 130 ml. of water is added dropwise thereto with stirring at 0°–5°C. over a period of 30 minutes. The resulting diazonium salt solution is stirred for an additional 15 minutes at 0°–5°C. A solution of 164 g. of potassium iodide in 700 ml. of 5-N sulfuric acid is subsequently added dropwise at 3°–6°C. over a period of 45 minutes. The entire mixture is stirred at room temperature for 30 minutes and subsequently warmed slowly to reflux temperature. After boiling at reflux temperature for 2 hours, the mixture is cooled to room temperature. The separated brown crystals are removed by filtration and washed neutral with water. The filter cake is dried under reduced pressure, and there is obtained 2-iodo-4-methoxy-benzoic acid in the form of brown crystals having a melting point of 174°C.

411 G. of 2-iodo-4-methoxy-benzoic acid, 4 liters of methanol and 400 ml. of concentrated sulfuric acid are heated under reflux for 4 hours. The solution is evaporated under reduced pressure, treated with water and extracted with ether. The organic phase is washed successively with aqueous sodium thiosulfate and aqueous sodium bicarbonate and then dried over sodium sulfate. The solution is filtered, evaporated under reduced pressure, distilled, and there is obtained 2-iodo-4-methoxy-benzoic acid methyl ester having a boiling point of 95°–98°C./0.04 mm.

205 G. of 2-iodo-4methoxy-benzoic acid methyl ester, 400 ml. of methanol, 390 ml. of water and 95 g. of potassium hydroxide are stirred at 48°C. for 30 minutes. The solution is then concentrated under reduced pressure and acidified with aqueous hydrochloric acid. The yellow crystalline 2-iodo-4-methoxy-benzoic acid obtained is removed by filtration, washed neutral with water and dried, melting point 185°C.

A solution of 170 g. of potassium hydroxide in 1.6 liters of water is treated under a nitrogen atmosphere at 50°C. with 102 g. of 4-methylthio-thiophenol. The resulting mixture is stirred for an additional 15 minutes. The mixture is then treated with 2.4 g. of copper powder and 180 g. of 2-iodo-4-methoxy-benzoic acid and heated under reflux for 7 hours. The mixture is filtered while hot, acidified with concentrated hydrochloric acid, cooled and filtered. The residue is washed with water, dried under reduced pressure, and there is obtained 4-methoxy-6-[(4-methylthio-phenyl)-thio]-benzoic acid having a melting point of 202°–203°C.

190 G. of 4-methoxy-6[-(4'-methylthio-phenyl)-thio]-benzoic acid in 1.8 liters of absolute tetrahydrofuran are treated dropwise under a nitrogen atmosphere under reflux with 850 ml. of a 70% sodium dihydrobis(2-methoxyethoxy)-aluminate solution in benzene. The resulting mixture is boiled for an additional 30 minutes under reflux. After cooling to 5°C., the mixture is acidified with 500 ml. of 3-N hydrochloric acid and with concentrated hydrochloric acid and then extracted with ether. The organic phase is washed successively with water, 2-N aqueous sodium hydroxide solution and again with water and then dried over sodium sulfate, filtered and evaporated, whereby there is obtained 4-methoxy-6-[(4'-methylthio-phenyl)-thio]-benzyl alcohol as a brown oil.

165 G. of 4-methoxy-6-[(4'-methylthio-phenyl)-thio]-benzyl alcohol are dissolved in 550 ml. of absolute benzene and heated under reflux. The solution is treated dropwise over a period of 45 minutes with 62 ml. of thionyl chloride and then boiled for an additional 30 minutes. The mixture is evaporated under reduced pressure, and the residue is extracted three times with benzene. After concentration of the benzene solution, there is obtained 4-methoxy-6-[(4'-methylthio-phenyl)-thio]-benzyl chloride as a dark-brown oil.

51 G. of potassium cyanide in 110 ml. of water are heated under reflux for 9 hours with 186 g. of 4-methoxy-6-[(4'-methylthio-phenyl)-thio]-benzyl chloride in 270 ml. of ethanol. The ethanol is removed by distillation under reduced pressure. The residue is diluted with water and then extracted with ether. The ether extracts are washed with water, dried over sodium sulfate, evaporated, and there is obtained 4-methoxy-6-[(4'-methylthio-phenyl)-thio]-phenylacetonitrile as a dark-brown oil.

160 G. of 4-methoxy-6-[(4'-methylthio-phenyl)-thio]-phenylacetonitrile, 330 ml. of ethanol, 162 g. of potassium hydroxide and 330 ml. of water are heated under reflux for 8 hours. Subsequently, the ethanol is evaporated under reduced pressure. The residue is dissolved in about 2 liters of water. The solution is extracted with ether and the ether extract discarded. The aqueous solution is cooled and acidified with concentrated hydrochloric acid. The solution is extracted with benzene. The benzene phase is washed with water, dried over sodium sulfate, filtered, evaporated, and there is obtained crude 4-methoxy-6-[(4'-methylthio-phenyl)-thio]-phenylacetic acid which melts at 125°C. after recrystallization from benzene/hexane.

29.3 G. of 4-methoxy-6-[(4'-methylthio-phenyl)-thio]-phenylacetic acid are stirred under reflux for 17 hours with 150 g. of polyphosphoric acid and 600 ml. of toluene. The mixture is cooled to about 60°C. and the toluene solution decanted. The residue is treated with toluene and boiled with stirring. The aqueous residue is treated with ice and water, and then extracted with toluene. The combined toluene solutions are washed successively with water and aqueous sodium hydroxide solution, dried over sodium sulfate and concentrated under reduced pressure, whereby there is obtained 3-methoxy-8-methylthio-dibenzo[b,f]thiepin-10(11H)-one as a red oil. After recrystallization from acetone/hexane, this product is obtained in the form of crystals having a melting point of 127°C.

17.8 G. of 3-methoxy-8-methylthio-dibenzo[b,f]thiepin-10(11H)-one are suspended in 150 ml. of ethanol and treated with 3.8 g. of sodium borohydride. The mixture is stirred for 90 minutes, subsequently treated with water and extracted with ether. The organic phase is washed with water, dried over magnesium sulfate, evaporated, and there is obtained 10,11-dihydro-3-methoxy-8-methylthio-dibenzo-[b,f]thiepin- 10-ol having a melting point of 122°–124°C.

15.7 G. of 10,11-dihydro-3-methoxy-8-methylthio-dibenzo[b,f]thiepin-10-ol, 250 ml. of benzene and 6 g. of finely powdered calcium chloride are saturated with hydrogen chloride gas at 15°C. within 2.5 hours and then stirred for an additional 3 hours. After the addition of 0.8 g. of active carbon, the precipitate is removed by filtration and washed with benzene. The benzene phase is evaporated under reduced pressure, and there is obtained 10-chloro-10,11-dihydro-3-methoxy-8-methylthio-dibenzo[b,f]thiepin having a melting point of 120°–123°C.

EXAMPLE 2

Preparation of
1-[10,11-dihydro-3-methyl-8-fluoro-dibenzo[b,f]thiepin-10-yl]-4-(2-propynyl)-piperazine In a manner analogous to that described in Example 1, from 10-chloro-10,11-dihydro-3-methyl-8-fluoro-dibenzo[b,f]thiepin and N-(2-propynyl)- there is obtained 1-[10,11-dihydro-3-methyl-8-fluoro-dibenzo[b,f]thiepin-10-yl]-4-(2-propynyl)-piperazine, the dimethanesulfonate of which melts at 168°–174°C.

The 10-chloro-10,11-dihydro-3-methyl-8-fluoro-dibenzo[b,f]thiepin used as the starting material can be prepared from 2-iodo-4methyl-benzoic acid and 4-fluoro-thiophenol in a manner analogous to that described in Example 1.

EXAMPLE 3

Preparation of
1-[8-chloro-10,11-dihydro-3-methoxy-dibenzo[b,f]-thiepin-10-yl]-4-(2-propynyl)-piperazine In a manner analogous to that described in Example 1, from 8,10-dichloro-10,11-dihydro-3-methoxy-dibenzo[b,f]thiepin and N-(2-propynyl)-piperazine there is obtained 1-[8-chloro-10,11-dihydro-3-methoxy-dibenzo[b,f]thiepin-10-yl]-4-(2-propynyl)-piperazine, the dimethanesulfonate of which melts at 177°–180°C.

The 8,10-dichloro-10,11-dihydro-3-methoxy-dibenzo[b,f]thiepin used as the starting material can be prepared from 2-iodo-4-methoxy-benzoic acid and 4-chlorothiophenol in a manner analogous to that described in Example 1. The following intermediates are obtained:

4-methoxy-2-[(4'-chloro-phenyl)-thio]-benzoic acid;
4-methoxy-2-[(4'-chloro-phenyl)-thio]-benzoic acid methyl ester having a melting point of 70°–72°C.;
4-methoxy-2-[(4'-chloro-phenyl)-thio]-benzyl alcohol having a melting point of 69°–70°C.;
4-methoxy-2-[(4'-chloro-phenyl)-thio]-benzyl chloride having a melting point of 61°–64°C.;
4-methoxy-2-[(4'-chloro-phenyl)-thio]-phenylacetonitrile (brown oil);
4-methoxy-2-[(4'-chloro-phenyl)-thio]-phenylacetic acid having a melting point of 115°–118°C.;
8-chloro-3-methoxy-dibenzo[b,f]thiepin-10(11H)-one having a melting point of 136°C.;
8-chloro-3-methoxy-dibenzo[b,f]thiepin-10-ol having a melting point of 105°–107°C.
The 8,10-dichloro-10,11-dihydro-3-methoxy-dibenzo[b,f]thiepin melts at 100°–102°C.

EXAMPLE 4

Preparation of
1-[8-fluoro-10,11-dihydro-2-methyl-dibenzo[b,f]thiepin-10-yl]-4-(2-propynyl)-piperazine 7 G. of 10-chloro-8-fluoro-10,11-dihydro-2-methyl-dibenzo[b,f]thiepin are heated under reflux for 20 hours with 7.8 g. of N-(2-propynyl)-piperazine and 40 ml. of chloroform. The chloroform is removed by evaporation and the residue is treated with ether and aqueous sodium hydroxide solution and mixed well. The ether phase is acidified with ethanolic hydrochloric acid. The precipitate which forms is removed by filtration, made alkaline with aqueous sodium hydroxide solution and taken up in benzene. The benzene phase is dried over sodium sulfate, evaporated, and there is obtained 1-[8-fluoro-10,11-dihydro-2-methyl-dibenzo[b,f]-thiepin-10-yl]-4-(2-propynyl)-piperazine which is converted into the dihydrochloride by reaction with ethanolic hydrogen chloride. The dihydrochloride melts at 230°–231°C.

The 10-chloro-8-fluoro-10,11-dihydro-2-methyl-dibenzo[b,f]thiepin used as the starting material can be prepared as follows:

A solution of 474.5 g. of potassium hydroxide in 3.6 liters of water is treated under a nitrogen atmosphere at 50°C. with 217 ml. of 4-fluoro-thiophenol and the mixture is stirred for 15 minutes at room temperature. After the addition of several grams of copper powder and of 536 g. of 2-iodo-5-methyl-benzoic acid, the mixture is heated under reflux for 7 hours. The mixture is filtered while hot, acidified with concentrated hydrochloric acid and again filtered. The residue is washed neutral with water, dried under reduced pressure, and there is obtained 3-methyl-6-[(4'-fluoro-phenyl)-thio]-benzoic acid having a melting point of 166°–167°C.

300 G. of 3-methyl-6-[(4'-fluoro-phenyl)-thio]-benzoic acid in 2 liters of absolute tetrahydrofuran are treated dropwise under a nitrogen atmosphere under reflux with 780 ml. of a 70% sodium dihydro-bis(2-methoxyethoxy)-aluminate solution in benzene and the mixture is heated under reflux for an additional hour. The mixture is cooled to 4°C. and acidified by the dropwise addition of 1300 ml. of 3-N hydrochloric acid. Then, the mixture is treated with concentrated hydrochloric acid and extracted with benzene. The organic phase is washed with water, dried over sodium sulfate, filtered, evaporated, and there is obtained 3-methyl-6-[(4'-fluoro-phenyl)-thio]-benzyl alcohol as a yellow oil.

337 G. of 3-methyl-6-[(4'-fluoro-phenyl)-thio]-benzyl alcohol are dissolved on 1 liter of absolute benzene and brought to reflux. The solution is treated dropwise with 190 ml. of thionyl chloride and boiled for an additional 45 minutes. The mixture is concentrated under reduced pressure. The residue is extracted several times with benzene. The combined benzene extracts are evaporated, and there is obtained 3-methyl-6-[(4'-fluoro-phenyl)-thio]-benzyl chloride as a brown oil.

115 G. of potassium cyanide in 150 ml. of water are heated under reflux for 10 hours with 344 g. of 3-methyl-6-[(4'-fluoro-phenyl)-thio]-benzyl chloride in 450 ml. of ethanol. The ethanol is then removed by distillation under reduced pressure. The residue is diluted with water and extracted with benzene. The benzene phase is washed with water, dried over sodium sulfate, evaporated, and there is obtained 3-methyl-6-[(4'-fluoro-phenyl)-thio]-phenylacetonitrile as a dark-brown oil.

106 G. of 3-methyl-6-[(4'-fluoro-phenyl)-thio]-phenyl acetonitrile, 300 ml. of ethanol, 100 g. of potassium hydroxide and 300 ml. of water are heated under reflux for 5 hours. The ethanol is then evaporated under reduced pressure. The residue is dissolved in water and the neutral constituents are extracted with benzene. The aqueous solution is acidified with concentrated hydrochloric acid and extracted with ethyl acetate. The organic phase is washed with water, dried over sodium sulfate, filtered, evaporated under reduced pressure, and there is obtained 3-methyl-6-[(4'-fluoro-phenyl)-thio]-phenylacetic acid as a dark-brown oil which, after recrystallization from benzene/hexane, melts at 117°C.

1810 G. of polyphosphoric acid are heated to 128°C. under a nitrogen atmosphere, treated rapidly with 173.6 g. of 3-methyl-6-[(4'-fluoro-phenyl)-thio]-phenylacetic acid and stirred at 120°–130°C. for 10 minutes. After the addition of ice chips, the mixture is extracted with benzene. The organic phase is washed successively with water and a saturated aqueous sodium carbonate solution, dried over sodium sulfate and evaporated, whereby there is obtained 8-fluoro-2-methyl-dibenzo[b,f]thiepin-10(11H)-one which melts at 103°–104°C.

103 G. of 8-fluoro-2-methyl-dibenzo[b,f]thiepin-10(11H)-one are suspended on 550 ml. of ethanol and treated with 24.3 g. of sodium borohydride. The mixture is heated under reflux for about 10 minutes. After the addition of water, the mixture is extracted with chloroform. The organic phase is washed with water, dried over sodium sulfate, evaporated, and there is obtained 8-fluroo-10,11-dihydro-2-methyl-dibenzo[b,f]thiepin-10-ol as an oil.

103 G. of 8-fluoro-10,11-dihydro-2-methyl-dibenzo[b,f]thiepin-10-ol, 500 ml. of benzene and 38.4 g. of finely powdered calcium chloride are saturated with hydrogen chloride gas at 15°C. and stirred overnight. The precipitate is removed by filtration, washed with benzene, evaporated under reduced pressure, and there is obtained 10-chloro-8-fluoro-10,11-dihydro-2-methyl-dibenzo[b,f]-thiepin which melts at 63°–64°C.

EXAMPLE 5

Preparation of 4- 4-[8-fluoro-10,11-dihydro-2-methyl-dibenzo[b,f]-thiepin-10-yl]-1-piperazinyl -2-butyn-1-ol 11.3 G. of 1-[8-fluoro-10,11-dihydro-2-methyl-dibenzo[b,f]thiepin-10-yl]-piperazine, 0.48 g. of sodium iodide, 6.3 g. of potassium carbonate and 4.0 g. of 4-chloro-2-butyn-1-ol are stirred at room temperature for 78 hours in 80 ml. of absolute ethanol. The mixture is subsequently treated with water and toluene. The toluene phase is washed with sodium chloride solution, dried over sodium sulfate and evaporated. The residue obtained is chromatographed over aluminum oxide with chloroform. The resulting 4- 4- 8-fluoro-10,11-dihydro-2-methyl-dibenzo[b,f]thiepin-10-yl]-1-piperazinyl -2-butyn-1-ol is converted into the dihydrochloride by treatment with ethanolic hydrogen chloride. The dihydrochloride melts at 206°–208°C.

The 1-[8-fluoro-10,11-dihydro-2-methyl-dibenzo[b,f]thiepin-10-yl]-piperazine used as the starting material can be prepared as follows:

24 G. of 10-chloro-8-fluoro-10,11-dihydro-2-methyl-dibenzo[b,f]thiepin in 80 ml. of chloroform are heated under reflux for 20 hours with 38.4 g. of 1-carbethoxy-piperazine. The mixture is poured on to ice-water and extracted with chloroform. The organic phase is dried over magnesium sulfate, evaporated under reduced pressure, and there is obtained crude, oily 1-carbethoxy-4-[8-fluoro-10,11-dihydro-2-methyl-dibenzo[b,f]thiepin-10-yl]-piperazine.

24.5 G. of 1-carbethoxy-4-[8-fluoro-10,11-dihydro-2-methyl-dibenzo[b,f]thiepin-10-yl]-piperazine, 350 ml. of ethyleneglycol, 19 g. of potassium hydroxide and 15 ml. of water are heated at 160°C. for 1 hour. The mixture is poured into water and extracted with chloroform. The organic phase is washed with water, dried over magnesium sulfate, evaporated under reduced pressure, and there is obtained 1-[8-fluoro-10,11-dihydro-2-methyl-dibenzo[b,f]thiepin-10-yl]-piperazine as a light-brown oil.

EXAMPLE 6

Preparation of
4- 4-[10,11-dihydro-3-methoxy-8-methylthio-dibenzo[b,f]thiepin-10-yl]-1-piperazinyl -2-butyn-1-ol In a manner analogous to that described in Example 5, from 1-[10,11-dihydro-3-methoxy-8-methylthio-dibenzo[b,f]thiepin-10-yl]-piperazine and 4-chloro-2-butyn-1-ol there is obtained 4- 4-[10,11-dihydro-3-methoxy-8-methylthio-dibenzo-[b,f]thiepin-10-yl]-1-piperazinyl -2-butyn-1-ol, the dihydrochloride of which melts at 208°–210°C.

The 1-[10,11-dihydro-3-methoxy-8-methylthio-dibenzo[b,f]thiepin-10-yl]-piperazine used as the starting material can be prepared as follows:

150 G. of 4-methoxy-anthranilic acid are suspended at 0°C. in 2 liters of water and 80 ml. of concentrated hydrochloric acid. To this solution is added dropwise with stirring at 0°–5°C. over a period of 30 minutes a solution of 62 g. of sodium nitrite in 130 ml. of water. The resulting diazonium salt solution is stirred for an additional 15 minutes at 0°–5°C. A solution of 164 g. of potassium iodide in 700 ml. of 5-N sulfuric acid is subsequently added dropwise at 3°–6°C. over a period of 45 minutes. Then, the mixture is stirred at room temperature for 30 minutes and heated slowly to reflux. After boiling at reflux for 2 hours, the mixture is cooled to room temperature. The precipitated brown crystals are removed by filtration and washed neutral with water. The filter cake is dried under reduced pressure, and there is obtained 2-iodo-4-methoxy-benzoic acid as brown crystals having a melting point of 174°C.

411 G. of 2-iodo-4-methoxy-benzoic acid, 4 liters of methanol and 400 ml. of concentrated sulfuric acid are heated under reflux for 4 hours. The solution is evaporated under reduced pressure, treated with water and extracted with ether. The organic phase is washed successively with aqueous sodium sulfate and aqueous sodium bicarbonate and then dried over sodium sulfate. The sodium is filtered, evaporated under reduced pressure, distilled, and there is obtained 2-iodo-4-methoxy-benzoic acid methyl ester having a boiling point of 95°–98°C/0.04 mm.

205 G. of 2-iodo-4-methoxy-benzoic acid methyl ester, 400 ml. of methanol, 390 ml. of water and 95 g. of potassium hydroxide are stirred at 48°C. for 30 minutes. Then, the solution is concentrated under reduced pressure and acidified with aqueous hydrochloric acid. The resulting yellow, crystalline 2-iodo-4-methoxy-benzoic acid is removed by filtration, washed neutral with water and dried; melting point 185°C.

A solution of 170 g. of potassium hydroxide in 1.6 liters of water is treated under a nitrogen atmosphere at 50°C. with 102 g. of 4-methylthio-thiophenol. Then, the mixture is stirred for an additional 15 minutes. The mixture is treated with 2.4 g. of copper powder and 180 g. of 2-iodo-4-methoxy-benzoic acid and heated under reflux for 7 hours. The mixture is filtered while hot, acidified with concentrated hydrochloric acid, cooled and filtered. The residue is washed with water, dried under reduced pressure, and there is obtained 4-methoxy-6-[(4'-methylthio-phenyl)-thio]-benzoic acid having a melting point of 202°–203°C.

190 G. of 4-methoxy-6-[(4'-methylthio-phenyl)-thio]-benzoic acid in 1.8 liters of absolute tetrahydrofuran are treated dropwise under a nitrogen atmosphere under reflux with 850 ml. of a 70% sodium dihydrobis(2-methoxyethoxy)-aluminate solution in benzene. The resulting mixture is boiled under reflux for an additional 30 minutes. After cooling to 5°C, the mixture is acidified with 500 ml. of 3-N hydrochloric acid and with concentrated hydrochloric acid and then extracted with ether. The organic phase is washed successively with water, 2-N aqueous sodium hydroxide solution and water, dried over sodium sulfate, filtered and evaporated, whereby there is obtained 4-methoxy-6-[(4'-methylthio-phenyl)-thio]-benzyl alcohol as a brown oil.

165 G. of 4-methoxy- 6-[(4'-methylthio-phenyl)-thio]-benzyl alcohol are dissolved in 550 ml. of absolute benzene and heated under reflux. The solution is treated dropwise with 62 ml. of thionyl chloride over a period of 45 minutes and then boiled for an additional 30 minutes. The mixture is evaporated under reduced pressure, and the residue is extracted three times with benzene. After concentration of the benzene solution, there is obtained 4-methoxy-6-[(4'-methylthio-phenyl)-thio]-benzyl chloride as a dark-brown oil.

51 G. of potassium cyanide in 110 ml. of water are heated under reflux for 9 hours with 186 g. of 4-methoxy-6-[(4'-methylthio-phenyl)-thio]-benzyl chloride. The ethanol is removed by distillation under reduced pressure. The residue is diluted with water and extracted with ether. The ether extracts are washed with water, dried over sodium sulfate, evaporated, and there is obtained 4-methoxy-6-[(4'-methylthio-phenyl)-thio]-phenylacetonitrile as a dark-brown oil.

160 G. of 4-methoxy-6-[(4'-methylthio-phenyl)-thio]-phenylacetonitrile, 330 ml. of ethanol, 162 g. of potassium hydroxide and 330 ml. of water are heated under reflux for 8 hours. Then, the ethanol is evaporated under reduced pressure. The residue is dissolved in about 2 liters of water. The solution is extracted with ether and the ether extracts are discarded. The aqueous solution is cooled and acidified with concentrated hydrochloric acid. Thereafter, the solution is extracted with benzene. The benzene phase is washed with water, dried over sodium sulfate, filtered, evaporated, and there is obtained crude 4-methoxy-6-[(4'-methylthio-phenyl)-thio]-phenylacetic acid which melts at 125°C. after recrystallization from benzene/hexane.

29.3 G. of 4-methoxy-6-[(4'-methylthio-phenyl)-thio]-phenylacetic acid are stirred under reflux for 17 hours with 150 g. of polyphosphoric acid and 600 mg. of toluene. The mixture is cooled to about 60°C. and the toluene solution decanted. The residue is treated with toluene and boiled with stirring. The aqueous residue is treated with ice and water and extracted with toluene. The combined toluene solutions are washed successively with water and aqueous sodium hydroxide solution, dried over sodium sulfate and concentrated under reduced pressure, whereby there is obtained 3-methoxy-8-methylthio-dibenzo[b,f]thiepin-10(11H)-one as a red oil. After recrystallization from acetone/hexane, the product is obtained in the form of crystals which melt at 127°C.

17.8 G. of 3-methoxy-8-methylthio-dibenzo[b,f]thiepin-10(11H)-one are suspended in 150 ml. of ethanol and treated with 3.8 g. of sodium borohydride. The mixture is stirred for 90 minutes. Then, it is treated with water and extracted with ether. The organic phase is washed with water, dried over magnesium sulfate, evaporated, and there is obtained 10,11-dihydro-3- methoxy-8-methylthio-dibenzo[b,f]thiepin-10-ol having a melting point of 122°–124°C.

15.7 G. of 10,11-dihydro-3-methoxy-8-methylthio-dibenzo[b,f]thiepin-10-ol, 250 ml. of benzene and 6 g. of finely powdered calcium chloride are saturated with hydrogen chloride gas at 15°C. over a period of 2.5 hours and subsequently stirred for an additional 3 hours. After the addition of 0.8 g. of active carbon, the precipitate is removed by filtration and washed with benzene. The benzene phase is evaporated under reduced pressure, and there is obtained 10-chloro-10,11-dihydro-3-methoxy-8-methylthio-dibenzo[b,f]thiepin having a melting point of 120°–123°C.

The desired 1-[10,11-dihydro-3-methoxy-8-methylthio-dibenzo[b,f]thiepin-10-yl]-piperazine can be obtained from the compound prepared in the preceding paragraph in a manner analogous to that described in Example 5 via 1-carbethoxy-4-[10,11-dihydro-3-methoxy-8-methylthio-dibenzo[b,f]thiepin-10-yl]-piperazine.

EXAMPLE 7

Preparation of
4- 4-[8-chloro-10,11-dihydro-3-methoxy-dibenzo[b,f]thiepin-10-yl]-1-piperazinyl -2-butyn-1-ol In a manner analogous to that described in Examples 5, from 1-[8-chloro-10,11-dihydro-3-methoxy-dibenzo[b,f]thiepin-10-yl]-piperazine and 4-chloro-2-butyn-1-ol, there is obtained 4- 4-[8-chloro-10,11-dihydro-3-methoxy-dibenzo-[b,f]thiepin-10-yl]-1-piperazinyl -2-butyn-1-ol, the dihydrochloride of which melts at 213°–215°C.

The 1-[8-chloro-10,11-dihydro-3-methoxy-dibenzo[b,f]thiepin-10-yl]-piperazine used as the starting material can be prepared in a manner analogous to that described in Example 5 from 8,10-dichloro-10,11-dihydro-3-methoxy-dibenzo-[b,f]thiepin via 1-carbethoxy-4-[8-chloro-10,11-dihydro-3-methoxy-dibenzo[b,f]-thiepin-10-yl]-piperazine.

The following Example illustrates a pharmaceutical preparation containing a dibenzo[b,f]thiepin derivative of formula I of the invention

EXAMPLE A

Tablets of the following composition are prepared

| | |
|---|---|
| 1-[10,11-Dihydro-3-methoxy-8-methylthio-dibenzo[b,f]thiepin-10-yl]-4-(2-propynyl)-piperazine dihydrochloride | 25.00 mg. |
| Lactose | 110.00 mg. |
| Maize starch | 61.00 mg. |
| Talc | 3.40 mg. |
| Magnesium stearate | 0.60 mg. |
| | 200.00 mg. |

The 1-[10,11-dihydro-3-methoxy-8-methylthio-dibenzo[b,f]thiepin-10-yl]-4-(2-propynyl)-piperazine dihydrochloride and the other ingredients are intimately mixed with one another and pressed into tablets each weighing 200 mg. The tablets are subsequently coated with ethyl cellulose and carbowax.

We claim:
1. A compound of the formula

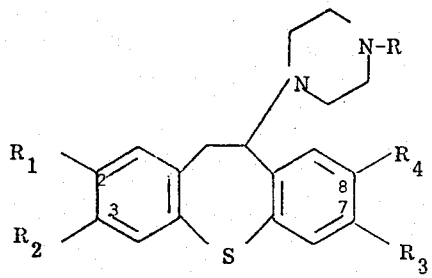

wherein R is lower alkynylalkyl, hydroxy-lower alkylalkynylalkyl or alkanoyloxy-lower alkylalkynylalkyl, and one of the two symbols $R_1$ and $R_2$ or $R_3$ and $R_4$ is hydrogen and the other is halogen, methyl, methoxy, methylthio, trifluoromethyl, methanesulfonyl or dimethylsulfamoyl, or a pharmaceutically acceptable acid addition salt thereof.

2. A compound in accordance with claim 1, wherein R is 2-propynyl or a pharmaceutically acceptable acid addition salt thereof.

3. A compound in accordance with claim 2, 1-[10,11-dihydro-3-methoxy-8-methylthio-dibenzo[b,f]-thiepin-10-yl]-4-(2-propynyl)-piperazine or a pharmaceutically acceptable acid addition salt thereof.

4. A compound in accordance with claim 2, 1-[8-chloro-10,11-dihydro-3-methoxy-dibenzo[b,f]thiepin-10-yl]-4-(2-propynyl)-piperazine or a pharmaceutically acceptable acid addition salt thereof.

* * * * *